US010085691B2

(12) United States Patent
Wu

(10) Patent No.: US 10,085,691 B2
(45) Date of Patent: Oct. 2, 2018

(54) WEARABLE DEVICE FOR SENSING PHYSIOLOGICAL INFORMATION

(71) Applicant: ASUSTeK COMPUTER INC., Taipei (TW)

(72) Inventor: Tung-Ke Wu, Taipei (TW)

(73) Assignee: ASUSTeK COMPUTER INC., Taipei (TW)

( * ) Notice: Subject to any disclaimer, the term of this patent is extended or adjusted under 35 U.S.C. 154(b) by 327 days.

(21) Appl. No.: 14/819,447

(22) Filed: Aug. 6, 2015

(65) Prior Publication Data

US 2017/0035353 A1 Feb. 9, 2017

(51) Int. Cl.
*A61B 5/00* (2006.01)
*A61B 5/024* (2006.01)
*G06F 1/16* (2006.01)

(52) U.S. Cl.
CPC .......... *A61B 5/6801* (2013.01); *A61B 5/0059* (2013.01); *A61B 5/02416* (2013.01); *A61B 5/681* (2013.01); *A61B 5/6802* (2013.01); *A61B 5/72* (2013.01); *A61B 5/725* (2013.01); *A61B 5/7235* (2013.01); *A61B 5/7257* (2013.01);
(Continued)

(58) Field of Classification Search
CPC .... A61B 2560/0209; A61B 2562/0219; A61B 5/0059; A61B 5/0075; A61B 5/68; A61B 5/681; A61B 5/6801; A61B 5/6802; A61B 5/6803; A61B 5/6804; A61B 5/6805; A61B 5/6806; A61B 5/6807; A61B 5/6808; A61B 5/6811; A61B 5/6812; A61B 5/6813; A61B 5/6814; A61B 5/6815; A61B 5/6819; A61B 5/6821; A61B 5/6822; A61B 5/6823; A61B 5/6824; A61B 5/6825; A61B 5/6826; A61B 5/6828; A61B 5/6829; A61B 5/683; A61B 5/6831; A61B 5/6832; A61B 5/6833; A61B 5/6835; A61B 5/6838; A61B 5/6839; A61B 5/72; A61B 5/7209; A61B 5/7221; A61B 5/7235; A61B 5/725; A61B 5/7253;
(Continued)

(56) References Cited

U.S. PATENT DOCUMENTS 6,491,647 B1 * 12/2002 Bridger .............. A61B 5/021
128/900
2007/0088221 A1 * 4/2007 Stahmann ........... A61B 5/0205
600/485
(Continued)

FOREIGN PATENT DOCUMENTS

CN 1711963 12/2005
CN 103581443 2/2014

*Primary Examiner* — Gordon J Stock, Jr.
(74) *Attorney, Agent, or Firm* — JCIPRNET

(57) ABSTRACT

A wearable device is provided. The wearable device includes an optical sensor and a controller. The optical sensor is adapted to emit at least one optical signal, and receive at least one reflective signal corresponding to the at least one optical signal. The at least one reflective signal includes a physiological information. The controller is coupled to the optical sensor, and includes a signal filter. The signal filter is adapted to perform a signal processing operation to the at least one reflective signal according to at least one signal processing parameter. The controller adjusts the at least one signal processing parameter of the signal filter according to the physiological information. A method of operating the wearable device is also provided.

21 Claims, 13 Drawing Sheets

(52) U.S. Cl.
CPC ............ *G06F 1/163* (2013.01); *A61B 5/7225* (2013.01); *A61B 5/7285* (2013.01); *A61B 2560/0209* (2013.01); *A61B 2562/0219* (2013.01)

(58) Field of Classification Search
CPC ... A61B 5/7289; A61B 5/7292; A61B 5/7225; A61B 5/7257; A61B 5/7285; G06F 1/163
See application file for complete search history.

(56) References Cited

U.S. PATENT DOCUMENTS

| | | | | |
|---|---|---|---|---|
| 2014/0275852 A1* | 9/2014 | Hong | .................. | A61B 5/02427 600/301 |
| 2014/0275854 A1* | 9/2014 | Venkatraman | ......... | A61B 5/721 600/301 |
| 2014/0278220 A1* | 9/2014 | Yuen | ....................... | G01B 21/16 702/150 |
| 2014/0343448 A1* | 11/2014 | Russell | ................ | A61B 5/0816 600/536 |
| 2015/0371028 A1* | 12/2015 | Patel | ....................... | G06F 21/44 726/16 |
| 2016/0066835 A1* | 3/2016 | He | ....................... | A61B 5/6898 482/4 |
| 2016/0317052 A1* | 11/2016 | Pan | ....................... | A61B 5/7257 |
| 2016/0345844 A1* | 12/2016 | McCombie | .......... | A61B 5/7221 |
| 2017/0100060 A1* | 4/2017 | Banet | .................. | A61B 5/0816 |

* cited by examiner

WEARABLE DEVICE FOR SENSING PHYSIOLOGICAL INFORMATION

BACKGROUND OF THE INVENTION

1. Field of the Invention

The present invention generally relates to a wearable device and a method of operating the wearable device.

2. Description of Related Art

Development of wearable devices or computers is accelerating with advances in technologies. Here, wearable devices refer to electronic devices that a user may naturally wear, like clothes, watches, glasses, and accessories. Wearable devices may achieve better portability than smartphones or tablet computers.

In particular, as one kind of wearable devices, a variety of products of a wrist watch, i.e. of a smart watch, has appeared. Generally, a conventional smart watch will utilize an accelerometer to determine whether the smart watch is in a static state. However, a smart watch being in a static state could mean different usage statuses, such as sitting on a table, or the user being asleep. An accelerometer by itself is unable to precisely determine the different usage statuses of a smart watch in a static state.

SUMMARY OF THE INVENTION

The invention provides a wearable device and an operating method of the wearable device.

A wearable device includes an optical sensor and a controller. The optical sensor is adapted to emit at least one optical signal, and receive at least one reflective signal corresponding to the at least one optical signal. The controller is coupled to the optical sensor, and is adapted to perform a signal processing operation to the at least one reflective signal according to at least one signal processing parameter.

A method of operating a wearable device includes emitting at least one optical signal, and receiving at least one reflective signal corresponding to the at least one optical signal through an optical sensor. Next, a signal processing operation is performed to the at least one reflective signal according to at least one signal processing parameter through the controller.

Based on the above, in the wearable device and the operating method thereof, since the signal processing parameter is adjusted according to the physiological information, the signal processing operation may produce more precise results.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
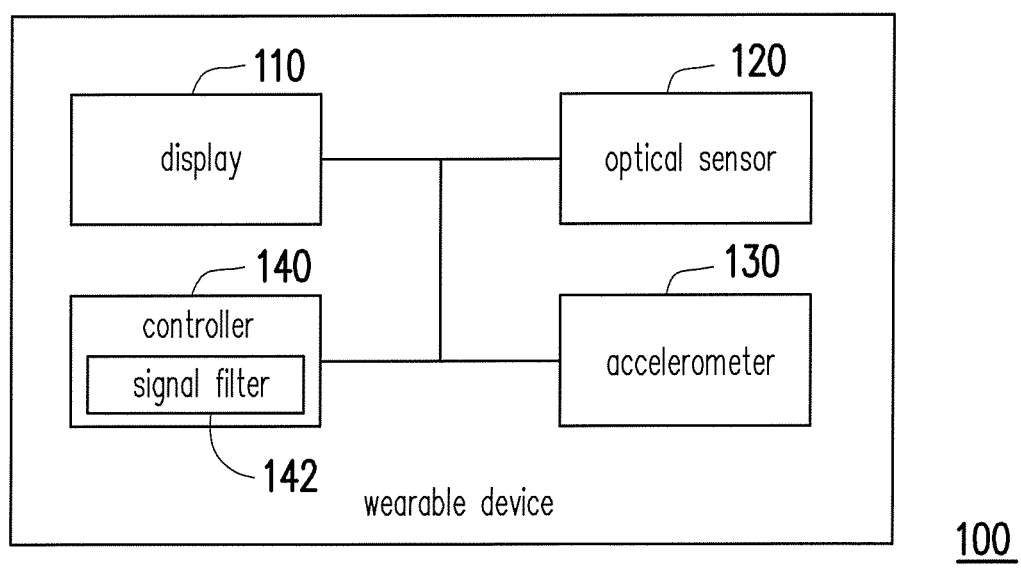
FIG. 1 is a block diagram of a wearable device of according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

Figure 2:
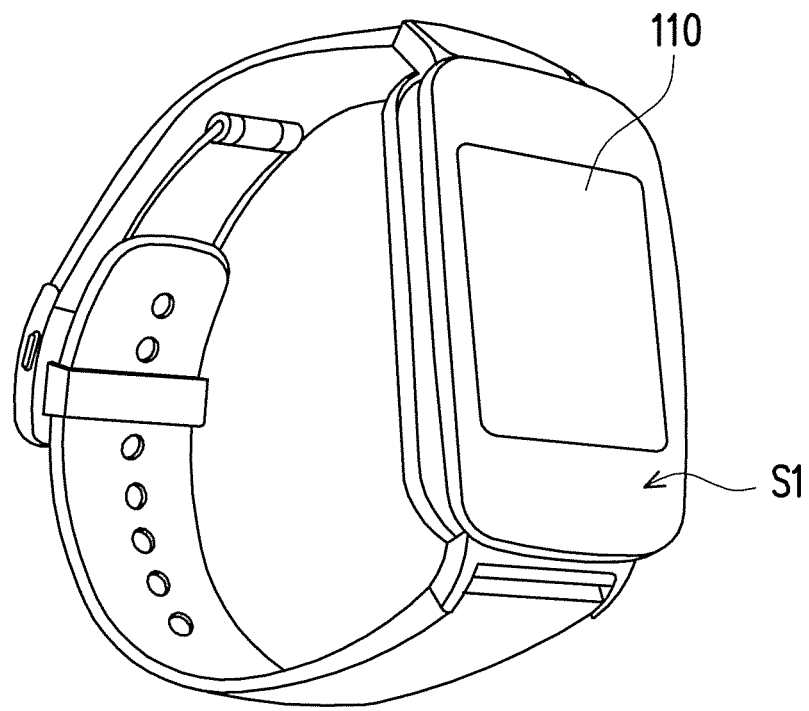
FIG. 2 is a front perspective view of a wearable device according to an embodiment of the invention.
Figure 3:
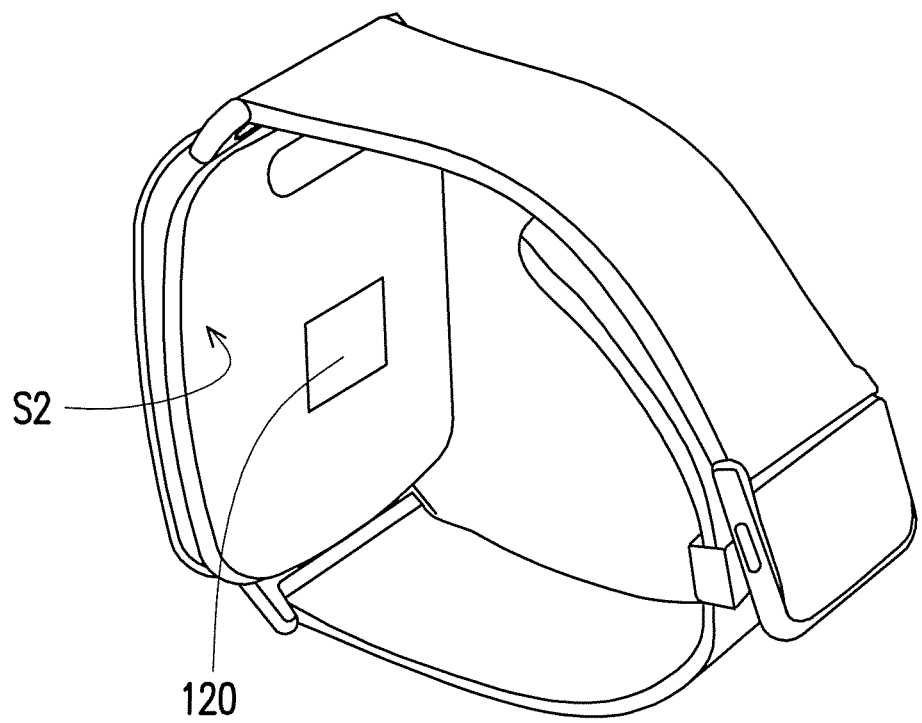
FIG. 3 is a back perspective view of the wearable device of FIG. 2.
Figure 4:
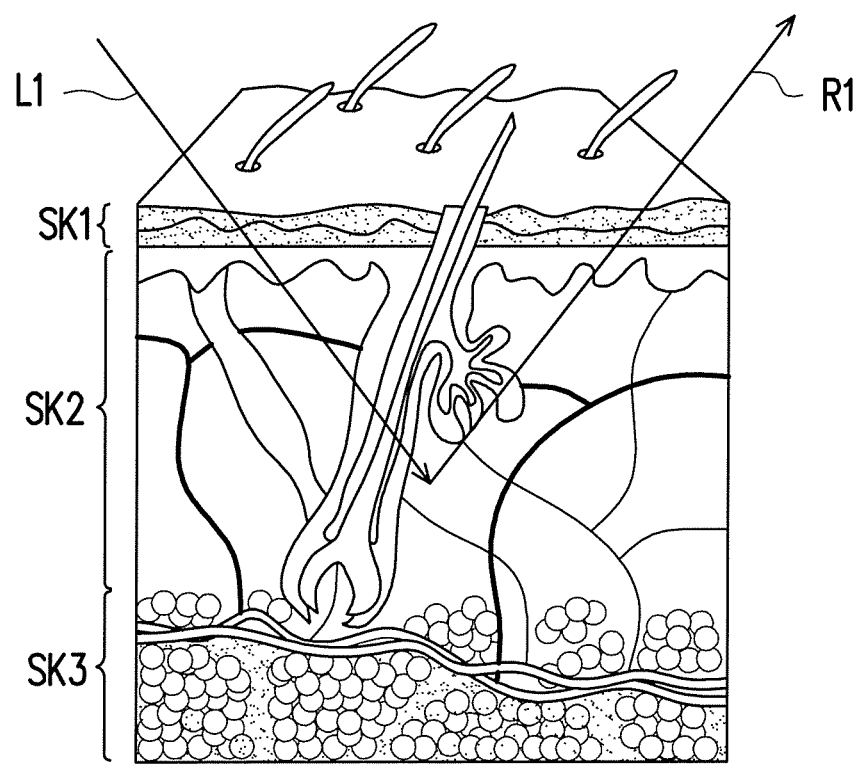
FIG. 4 is partial diagram of a test object according to an embodiment of the invention.

FIG. 1 is a block diagram of a wearable device of according to an embodiment of the invention. FIG. 2 is a front perspective view of a wearable device according to an embodiment of the invention. FIG. 3 is a back perspective view of the wearable device of FIG. 2. FIG. 4 is a partial diagram of a test object according to an embodiment of the invention. Referring to FIG. 1 to FIG. 4, a wearable device 100 includes a display 110, an optical sensor 120, an accelerometer 130, and a controller 140. The wearable device 100 is, for example, a smart watch. As seen in FIG. 2 and FIG. 3, the wearable device 100 may be worn on a wrist of a user. However, the invention is not limited thereto, and the wearable device 100 may be any other type of wearable computer or electronic device according to one of ordinary skill in the art. The wearable device 100 may also be worn on a user's foot, arm, neck, waist, etc. Where the wearable device 100 is worn may be applied differently according to one of ordinary skill in the art.

In the embodiment, the display 110 is coupled to the controller 140 and is located on a front surface S1 of the wearable device 100. The controller 140 controls the display 110 to display information such as time, weather information, physiological information, etc. The display 110 may be a touch display. However, the invention is not limited thereto. The display 100 may also be a non-touch display. In addition, the type of the display 110 utilized in the wearable device 100 may be selected according to one of ordinary skill in the art. For example, the display 110 may be a light-emitting diode display, a liquid crystal display, an organic light-emitting diode display, a plasma display, etc. The invention does not limit the type of the display 110 utilized in the wearable device 100.

The accelerometer 130 is coupled to the controller 140, and is located in the wearable device 100. The type of the accelerometer 130 utilized in the wearable device 100 may be selected according to one of ordinary skill in the art. For example, the accelerometer 130 may be an optical accelerometer, a piezoelectric accelerometer, a resonance accelerometer, etc. The invention does not limit the type of the accelerometer 130 utilized in the wearable device 100.

The optical sensor 120 is coupled to the controller 140 and located on a back surface S2 of the wearable device 100. The optical sensor 120 may be, for example, a square shape. However, the invention is not limited thereto. The optical sensor 120 may be other shapes such as a triangle, circle, or other shape according to one of ordinary skill in the art.

The accelerometer 130 is adapted to detect an acceleration of the wearable device 100. The controller 140 determines if the wearable device 100 is in a static state according to a sensing result of the accelerometer 130. For example, the accelerometer 130 continuously senses if there is an acceleration of the wearable device 100. If there is an acceleration of the wearable device 100, then the wearable device 100 is in a dynamic state, and not a static state. If the accelerometer 130 does not detect any acceleration, then the controller 140 determines if the wearable device 100 has no acceleration for a predetermined time. The predetermined time may be for example, a few minutes. However, the predetermined time may be any amount of time adjusted according to one of ordinary skill in the art. Once the wearable device 100 has no acceleration exceeding the predetermined time, the controller 140 determines that the wearable device 100 is in a static state.

Referring to FIG. 4, if the wearable device 100 is in the static state, the controller 140 controls the optical sensor 120 to emit at least one optical signal L1, and receive at least one reflective signal R1. That is to say, the optical sensor 120 is adapted to emit at least one optical signal L1, and receive at least one reflective signal R1 which corresponds to the optical signal L1. The reflective signal R1 may include physiological information.

In particular, the optical sensor 120 receives the at least one reflective signal R1 with different intensities when corresponding and reflecting off of different test objects. As seen in FIG. 4, for example, the at least one optical signal L1 is emitted toward the test object, for example, skin of the user. It can be seen that the at least one optical signal L1 penetrates through the skin. That is to say, the at least one optical signal L1 penetrates through the epidermis SK1 of the skin, and is reflected off the dermis SK2 of the skin to become the at least one reflective signal R1 including the physiological information. However, the invention is not limited thereto. Depending on the physiological information that is desired to be obtained, the at least one optical signal L1 may reflect off the epidermis SK1 of the skin without penetrating to the dermis SK2. Or, the at least one optical signal L1 may penetrate through the epidermis SK1, the dermis SK2, and a hypodermis SK3 of the skin to reflect off the hypodermis SK3. How far the at least one optical signal L1 penetrates through the skin of the user may be determined according to one of ordinary skill in the art. Furthermore, if the at least one optical signal L1 is emitted toward a test object that is not associated with a human, such as a table, it may not include physiological information.

Figure 5:
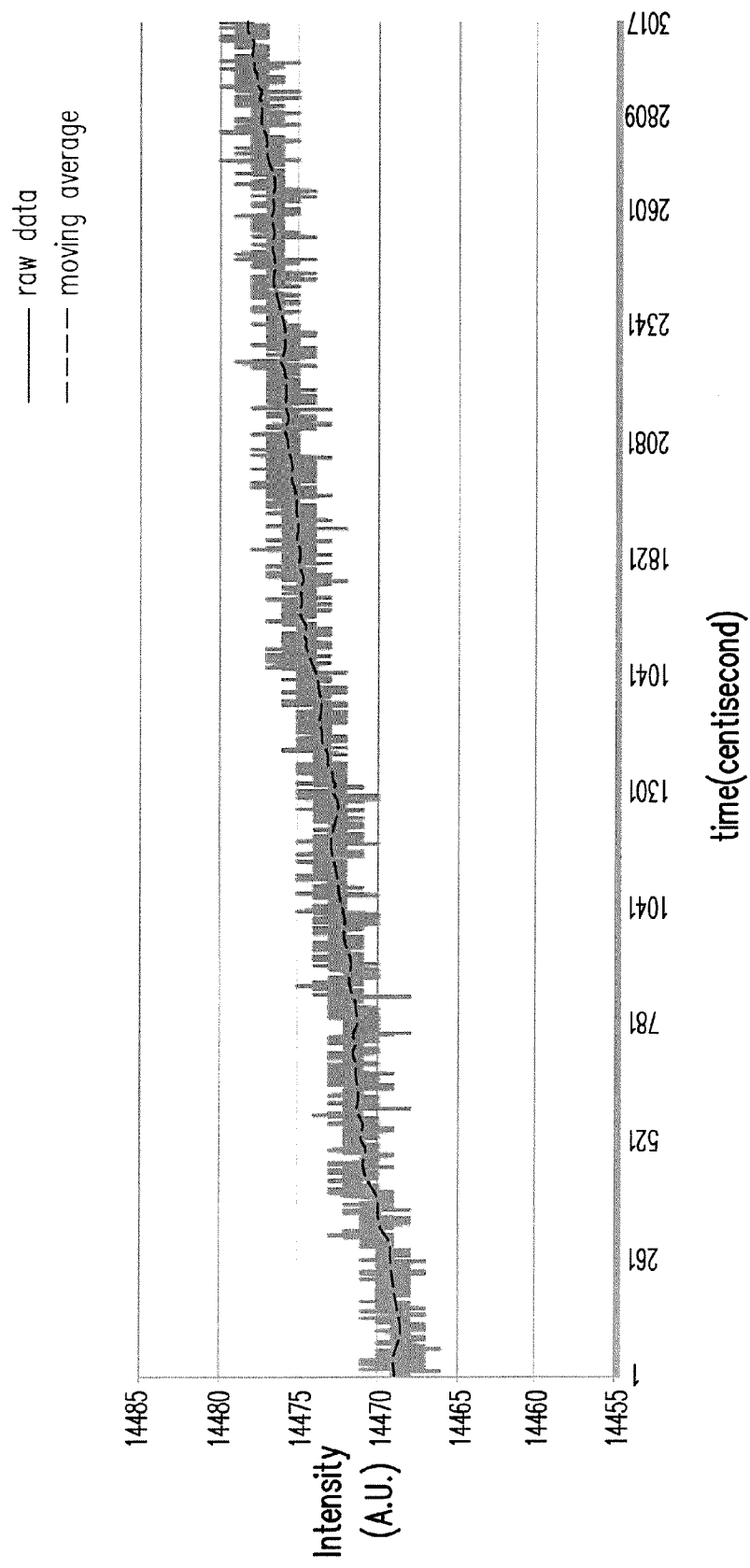
FIG. 5 is a graph showing the data read by the optical sensor when the wearable device of FIG. 1 is placed on a table.

FIG. 5 is a graph showing the data read by the optical sensor when the wearable device of FIG. 1 is placed on a table. FIG. 5 is only an exemplary figure, and the data of when the wearable device 100 is placed on a table is not limited to the data in FIG. 5. The y-axis shows the intensity in arbitrary units, and the x-axis shows the time in centiseconds. That is to say, the graph of FIG. 5 shows the data of the reflective signal R1 read by the optical sensor 120 after the reflective signal R1 has been reflected off a table. The graph of FIG. 5 shows the actual raw data, and also a smoothed moving average of the raw data. Specifically, the controller 140 performs a signal processing operation that includes calculating the raw data of the reflective signal R1 in order to obtain the smoothed moving average.

Figure 6:
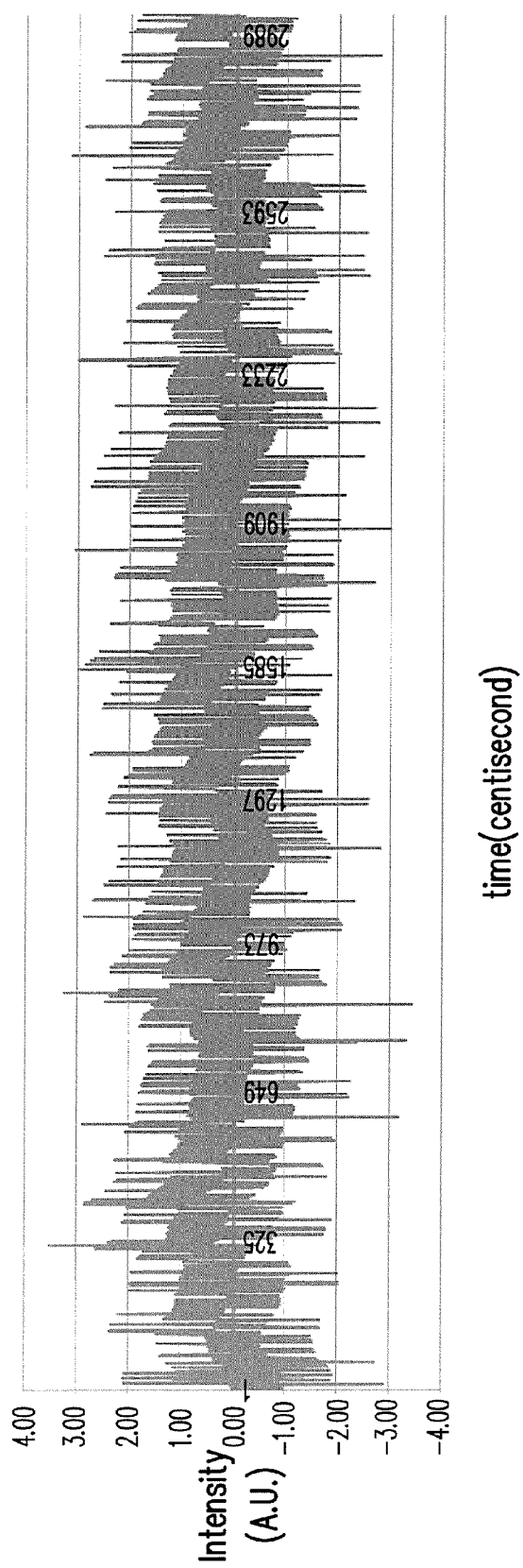
FIG. 6 is a graph of the difference between the raw data and the moving average of FIG. 5.

FIG. 6 is a graph of the difference between the raw data and the moving average of FIG. 5. The controller 140 further performs the signal operation to subtract the moving average from the raw data in order to obtain the data in FIG. 6. That is to say, FIG. 6 shows the data of FIG. 5 with the raw data subtracting the moving average. It can be seen from FIG. 5 and FIG. 6 that when the wearable device 100 is placed on a table, the data of the reflective signal R1 read by the optical sensor 120 is close to white noise. The calculation done by the controller 140 to obtain FIG. 5 and FIG. 6 are done in a time domain.

Figure 7:
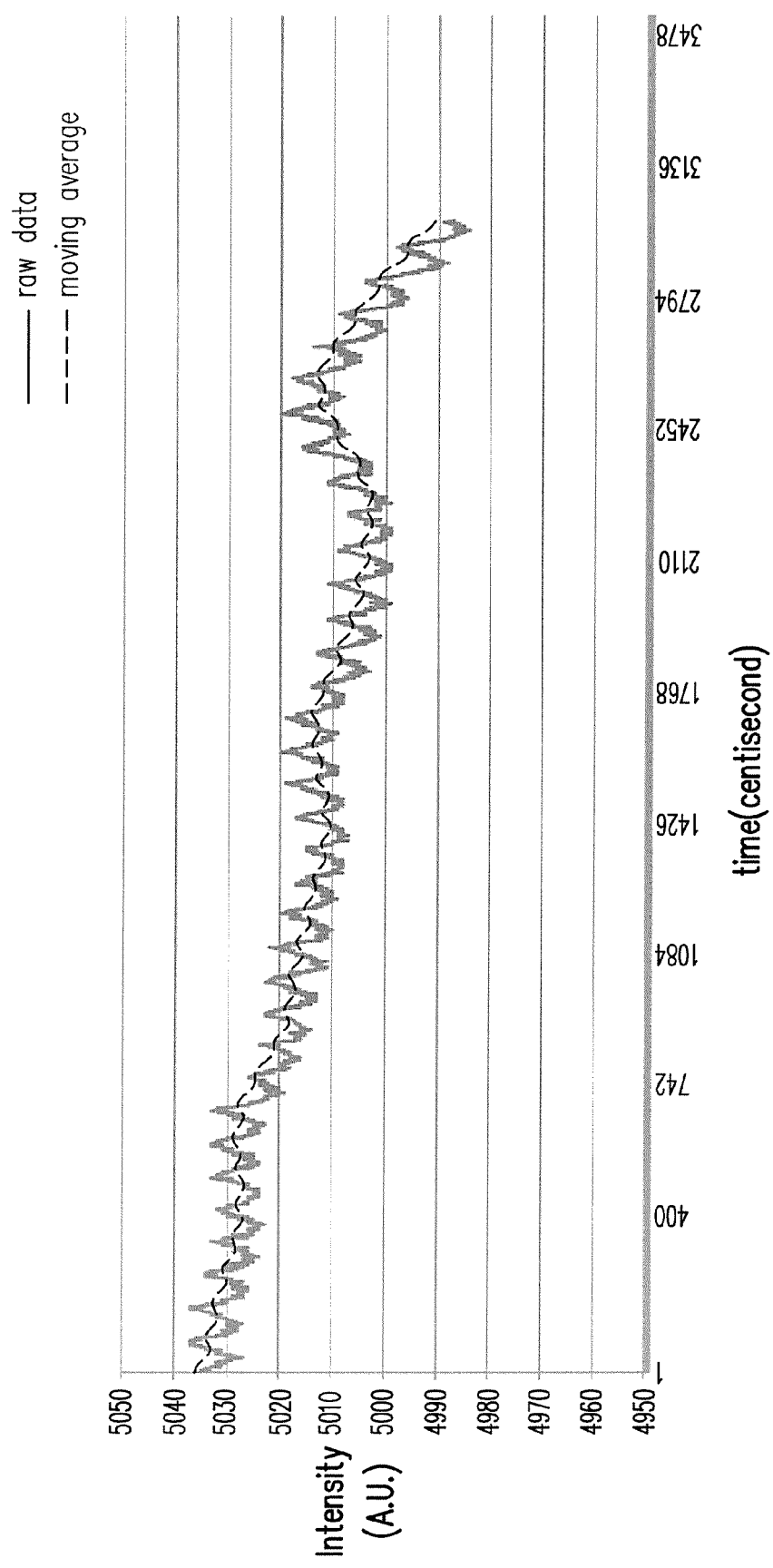
FIG. 7 is a graph showing the data read by the optical sensor when the wearable device of FIG. 1 is worn by a user.

FIG. 7 is a graph showing the data read by the optical sensor when the wearable device of FIG. 1 is worn by a user. FIG. 7 is only an exemplary figure, and the data of when the wearable device 100 is worn by a user is not limited to the data in FIG. 7. The y-axis shows the intensity in arbitrary units, and the x-axis shows the time in centiseconds. That is to say, the graph of FIG. 7 shows the data of the reflective signal R1 read by the optical sensor 120 after the reflective signal R1 has been reflected off the skin of a user. The graph of FIG. 7 shows the actual raw data, and also a smoothed moving average of the raw data. Specifically, the controller 140 performs a signal processing operation that includes calculating the raw data of the reflective signal R1 in order to obtain the smoothed moving average. In the embodiment, the smoothed moving averages of FIG. 5 and FIG. 7 are calculated through linear smoothing. However, the invention is not limited thereto, and the smoothed moving average may be calculated through any other type of smoothing algorithm according to one of ordinary skill in the art.

Figure 8:
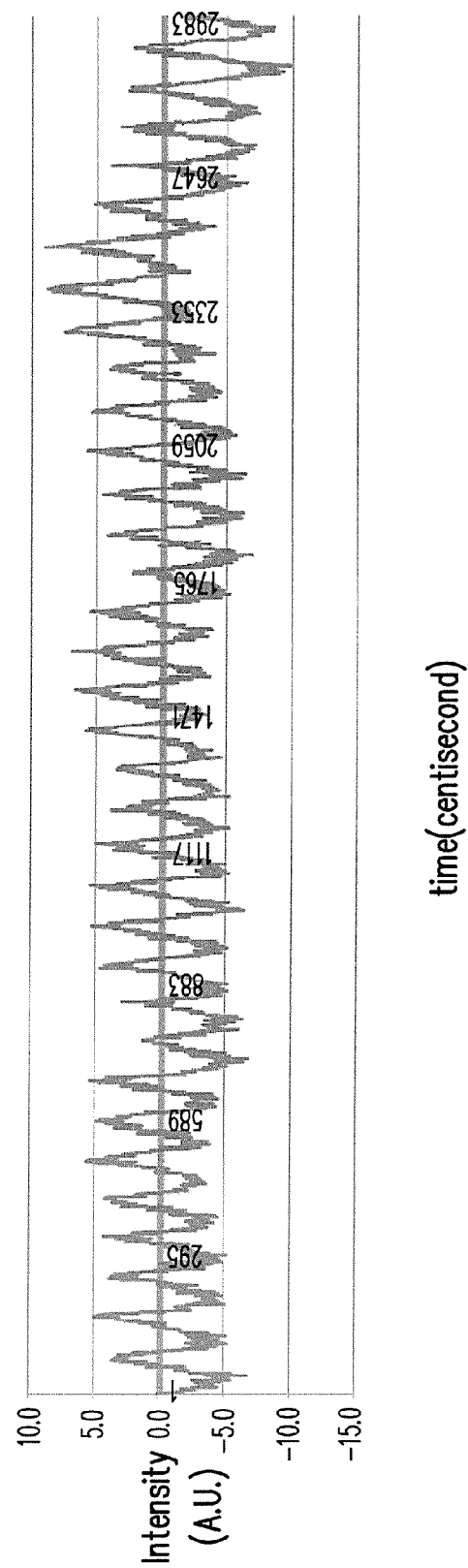
FIG. 8 is a graph of the difference between the raw data and the moving average of FIG. 7.

FIG. 8 is a graph of the difference between the raw data and the moving average of FIG. 7. The controller 140 further performs the signal processing operation to subtract the moving average from the raw data in order to obtain the data in FIG. 8. That is to say, FIG. 8 shows the data of FIG. 7 with the raw data subtracting the moving average. It can be seen from FIG. 7 and FIG. 8 that when the wearable device 100 is worn by the user, the data of the reflective signal R1 read by the optical sensor 120 includes physiological information, and is much clearer and more distinguishable compared to the data in FIG. 5 and FIG. 6. The calculation done by the controller 140 to obtain FIG. 7 and FIG. 8 are done in a time domain.

In the embodiment, the controller 140 further performs the signal processing operation to the at least one reflective signal R1 according to at least one signal processing parameter. In particular, the signal processing operation may be determining if the at least one reflective signal R1 is higher than a predetermined threshold value. In the embodiment, if the at least one reflective signal R1 is higher than the predetermined threshold value, then a status that the user is wearing the wearable device 100. If the at least one reflective signal R1 is lower than the predetermined threshold value, then a status that the user is not wearing the wearable device 100.

Referring to FIG. 6 and FIG. 8, the controller 140 performs the signal processing operation to the data of the reflective signal R1 shown in either FIG. 6 or FIG. 8. The signal processing operation would determine that the data in FIG. 6 is lower than a predetermined threshold value, indicating that the user is not wearing the wearable device 100. The signal processing operation would determine that the data in FIG. 8 is higher than a predetermined threshold value, indicating that the user is wearing the wearable device 100. However, the invention is not limited thereto. The predetermined threshold may allow the controller 140 to determine other usage statuses of the wearable device 100 according to one of ordinary skill in the art.

Alternatively, the signal processing operation may be further performing a Fast Fourier transformation (FFT) to the data of the reflective signal R1, such as the data in either FIG. 6 or FIG. 8. Performing FFT to the data of the reflective signal R1 may allow the controller 140 to determine if there is a specific peak frequency within a predetermined frequency range. For example, performing FFT to the data of FIG. 6, which is close to white noise, would not produce a specific peak frequency at a predetermined frequency range. This may help determine a status that the user is not wearing the wearable device 100. In contrast, performing FFT to the data of FIG. 8, would produce a specific peak frequency at, for example, a frequency range from 0.6 Hz to 4 Hz. This may help determine another status that the user is wearing the wearable device 100.

In the embodiment, the at least one optical signal L1 includes a first optical signal and a second optical signal, respectively corresponding to the at least one reflective signal R1 including a first reflective signal and a second reflective signal. In the embodiment, the first optical signal and the second optical signal are alternately emitted. However, the invention is not limited thereto. The first optical signal and the second optical signal may be simultaneously or separately emitted. In the embodiment, the first reflective signal and the second reflective signal correspond to a test object by being reflected off the test object. As described above, the test object may be the skin of a user, a surface of a table, or something else. Since there are many different test objects, there will be a variation in the intensity of the first reflective signal and the second reflective signal when reflected off of different test objects. An intensity variation of the first reflective signal when reflecting off different types test objects is greater than an intensity variation of the second reflective signal when reflecting off different types of test objects. The different types of test objects may be, for example, users of different skin color. Thus, the controller 140 determines the physiological information of the test objects according to the different intensities of the first reflective signal. In the embodiment, the physiological information is, as stated above, for example, skin color. However, the invention is not limited thereto. The physiological information may be information such as weight, body-mass index, heartrate, etc.

For example, the first optical signal is a green light emitted from the optical sensor 120 and the first reflective signal is a green light reflected back to the optical sensor 120, wherein the first reflective signal is corresponding to the first optical signal. The test objects are the objects which the optical signals are emitted on. For example, the test objects may be the skin of a user wearing the wearable device 100 or a table that the wearable device 100 is sitting on. The different intensities of the green light reflected back to the optical sensor 120, or the first reflective signal has a large intensity variation between different test objects. For instance, the intensity reflected back to the optical sensor 120 from a dark-skinned user is lower than the intensities reflected back to the optical sensor 120 from a light-skinned user. This way, the optical sensor 120 may determine if the user is dark-skinned or light-skinned from the green light, or the first reflective signal. As a result, the race of the user (i.e. white, Asian, black, etc.) may be determined from the first reflective signal, or the green light. However, the invention is not limited thereto. The first reflective signal may also be directed to detect and determine other information and the optical sensor 120 may emit different types of light. That is to say, the optical sensor 120 may emit other colors of visible light, or other types of non-visible light.

In addition, the controller 140 determines a usage status of the wearable device 100 according to the different intensities of the second reflective signal. For example, the second optical signal is an infrared light emitted from the optical sensor 120 and the second reflective signal is an infrared light reflected back to the optical sensor 120, wherein the second reflective signal is corresponding to the second optical signal. In addition, the different intensities of the infrared light reflected back to the optical sensor 120, or the second reflective signal has a small intensity variation between different test objects. Therefore, the intensities reflected back from different skin colors will have small variation for infrared light. As such, it may be determined whether or not the intensities reflected back from the test object falls in a range of intensity values of skin or not. When the value of the intensity of the infrared light falls in the intensity range of skin, it may be determined that the user is wearing the wearable device 100. When the value of the intensity of the infrared light falls outside the intensity range of skin, it may be determined that the user is not wearing the wearable device 100, and that the wearable device may be, for example, sitting on a table. However, the invention is not limited thereto. The second reflective signal may also be directed to detect and determine other information and the optical sensor 120 may emit different types of light. That is to say, the optical sensor 120 may emit other colors of visible light, or other types of non-visible light.

Thus, it can be seen that the first optical signal and the second optical signal together determine the usage status of the wearable device 100 (i.e. user wearing the wearable device 100 or not), and the physiological information of the user. However, the invention is not limited thereto. The first optical signal and the second optical signal may be separately emitted to determine another usage status of the wearable device 100 or other information of the user. In addition, the invention is not limited to only two optical signals. The invention may utilize only one optical signal or three or more optical signals for different results depending on the accuracy and precision requirements according to one of ordinary skill in the art.

Figure 9:
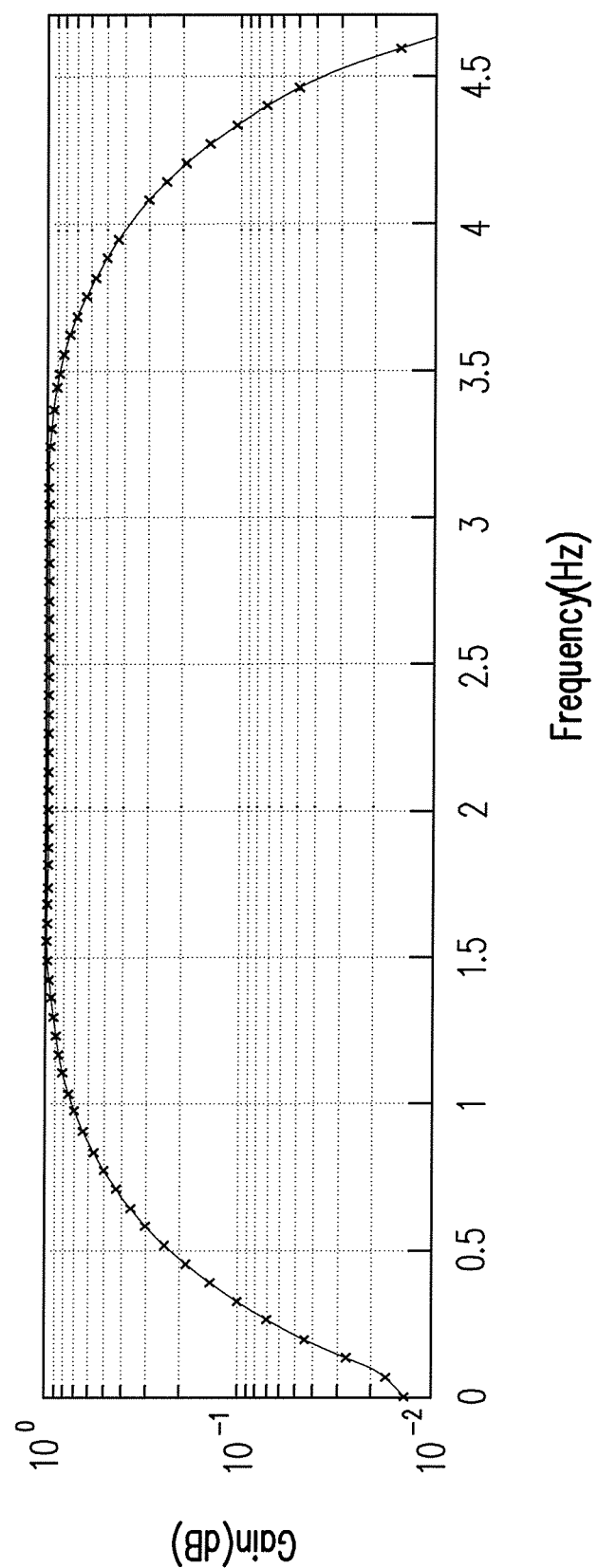
FIG. 9 is a graph of the signal filter according to an embodiment of the invention.
Figure 10:
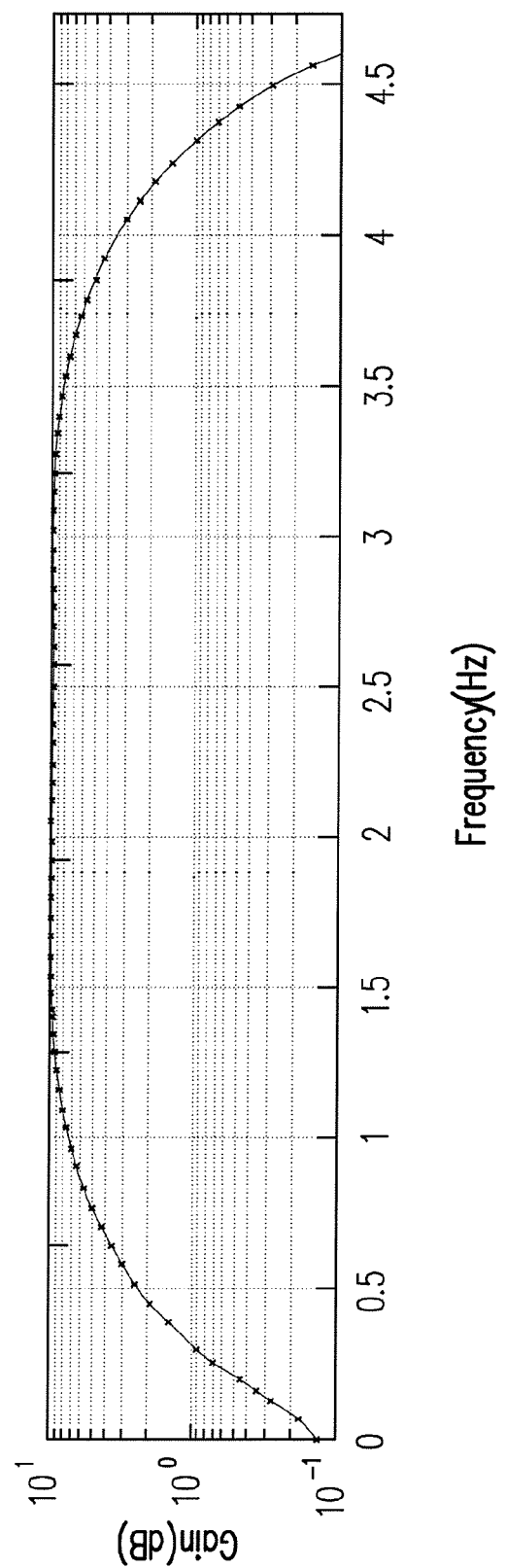
FIG. 10 is a graph of the signal filter according to another embodiment of the invention.

Referring to FIG. 9, FIG. 9 is a graph of a signal filter 142 of the embodiment. In the embodiment, the controller 140 further includes a signal filter 142. In the embodiment, the signal filter 142 may be, for example, a finite impulse response filter. However, the invention is not limited thereto. The signal filter 142 may also be, for example, an infinite impulse response filter, continuous-time filter, etc. The type of signal filter may be selected according to one of ordinary skill in the art. The signal filter 142 is adapted to perform the signal processing operation to the at least one reflective signal R1 according to at least one signal processing parameter. The graph in FIG. 9 shows the magnitude response of the signal filter 142, wherein the x-axis is the frequency, and the y-axis is the magnitude measured in decibels (dB). The gain in the graph of FIG. 9 is set at 10°, or 1. However, the invention is not limited thereto. The controller 140 adjusts the signal processing parameter of the signal filter 142 according to the physiological information. In another embodiment, as seen in FIG. 10, FIG. 10 is a graph that shows the magnitude response of the signal filter 142 with a gain of 10. The x-axis is also the frequency, and the y-axis is the magnitude with a gain of 10 measured in decibels (dB). Specifically, the controller 140 sets a signal gain of the signal filter 142 according to the physiological information, and the signal filter 142 performs the signal processing operation to the at least one reflective signal R1 according to the signal gain. Using skin color as an example of the physiological information, the skin color of a user affects the reflective signal, and so the signal gain is set according to the skin color. For example, the signal gain of a dark-skinned user may need to be higher than the signal gain of a light-skinned user. This is because the magnitude of the reflective signal of a dark-skinned user may be lower than the magnitude of the reflective signal of a light-skinned user. The signal gain increases the amplitude of the reflective signal so as to better read the reflective signal. This will provide more precise results in detecting and reading the reflective signal. Thus, since the signal filter 142 of FIG. 9 has a gain of 1, then the signal filter 142 is more suitable for, for example, a light-skinned user. Since the signal filter 142 of FIG. 10 has a gain of 10, then the signal filter 142 is more suitable for, for example, a dark-skinned user. However, the gain of the signal filter 142 is not limited to 1 or 10, but may be any other setting suitable according to the physiological information of the user. The controller 140 may also set a different gain of the signal filter 142 according to one of ordinary skill in the art.

In addition, the controller 140 also sets a frequency processing range of the signal filter 142 according to the physiological information of the user, and the signal filter 142 performs the signal processing operation to the at least one reflective signal R1 within the frequency processing range. In the embodiment, the physiological information is, for example, a heartrate of the user. That is to say, the signal filter 142 filters the at least one reflective signal R1 to be within the frequency processing range. In the embodiment, the frequency processing range is set to be a range of when the wearable device 100 is being worn by a user. Thus, as seen in FIG. 9 and FIG. 10, the frequency processing range may be set between 0.6 Hz to 4 Hz, which is around the range of a heartrate of a human. However, the frequency processing range may also be set as, for example, a range of when the user wearing the wearable device 100 is sleeping, which is between 0.6 Hz to 2 Hz, or around the range of a heartrate of a human that is sleeping. The frequency processing range of the signal filter 142 set by the controller 140 is not limited to that in FIG. 9 and FIG. 10, and may be other values determined by one of ordinary skill in the art.

Figure 11:
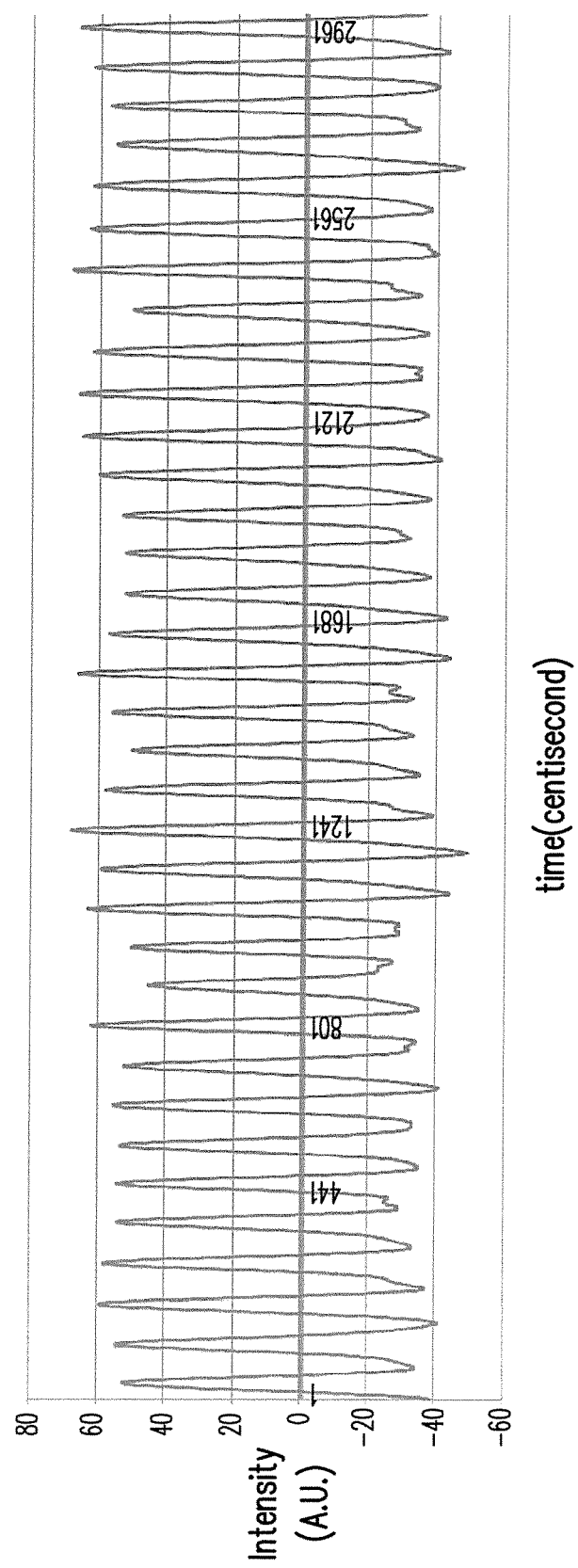
FIG. 11 is a graph showing the data of FIG. 7 after being processed by the signal filter of FIG. 10.

In particular, by filtering the reflective signal R1 with the signal filter 142 to be within in the frequency processing range, and applying a specific gain, the reflective signal R1 may be clearly seen within the frequency processing range. If the reflective signal R1 has a specific peak frequency within the frequency processing range, then the controller 140 may determine that the wearable device 100 is in a first usage status. However, if after the reflective signal R1 is filtered by the signal filter 142 and there is no specific peak frequency within the frequency range, the controller 140 determines that the wearable device 100 is in a second usage status. In the example of FIG. 9 and FIG. 10, if the frequency processing range is set to be between 0.6 Hz to 4 Hz, then the first usage status is, for example, the user wearing the wearable device 100. That is to say, the reflective signal R1 will have a specific peak frequency between 0.6 Hz to 4 Hz. The second usage status is, for example, the user not wearing the wearable device 100. This is because if the user is not wearing the wearable device 100 and the wearable device 100 is sitting on, for example, a table, the frequency of the reflective signal would be close to white noise, and there would be no specific peak frequency in the range of 0.6 Hz to 4 Hz. Referring to FIG. 11, FIG. 11 is a graph showing the data of FIG. 7 after being processed by the signal filter of FIG. 10. It can be seen in FIG. 11 that the reflective signal R1 has a specific peak frequency, and so the status of the wearable device 100 is the first usage status. If the frequency processing range is set to be between 0.6 Hz to 2 Hz, then the first usage status is, for example, the user wearing the wearable device 100 and sleeping. The second usage status is, for example, that the user is not sleeping or not wearing the wearable device 100. However, the invention is not limited thereto. The frequency processing range may be set in a range to determine other statuses of the wearable device 100. In the embodiment, it should be noted that the signal filter 142 performs filtering with respect to time. However, the invention is not limited thereto. In other embodiments, the signal filter 142 may perform filtering in a frequency domain.

In addition, after the signal filter 142 has filtered the at least one reflective signal R1 and amplified the at least one reflective signal R1 to produce a filtered signal, the controller 140 may further calculate, for example, a heartrate of the user. Since the gain of the signal filter 142 was set according to the physiological information, or skin color, of the user, the heartrate may be more precisely calculated. In detail, the skin color helps determine the race of the user, and the magnitude of the signal transmitted from users of different races may vary. A user of a white race may transmit a signal of a heartrate with a magnitude greater than a user of Asian race or black race. Therefore, the gain is set according to the race or skin color of the user, which may more precisely calculate the heartrate. If the heartrate of the user is determined, then the controller 140 may confirm that the user is wearing the wearable device 100. However, if the heartrate of the user cannot be determined after a predetermined amount of time, the controller 140 may confirm that the user is not wearing the wearable device. The predetermined amount of time may be, for example, 30 seconds. However, the invention is not limited thereto, and the predetermined amount of time may be adjusted according to one of ordinary skill in the art. The invention is not limited to calculating a heartrate of the user. The controller 140 may be designed according to one of ordinary skill in the art to calculate other information from the filtered signal such as pulse when sleeping, calories, and number of steps walked in a day, etc. The controller 140 may control the display 110 to display the heartrate or other information of the user.

Figure 12:
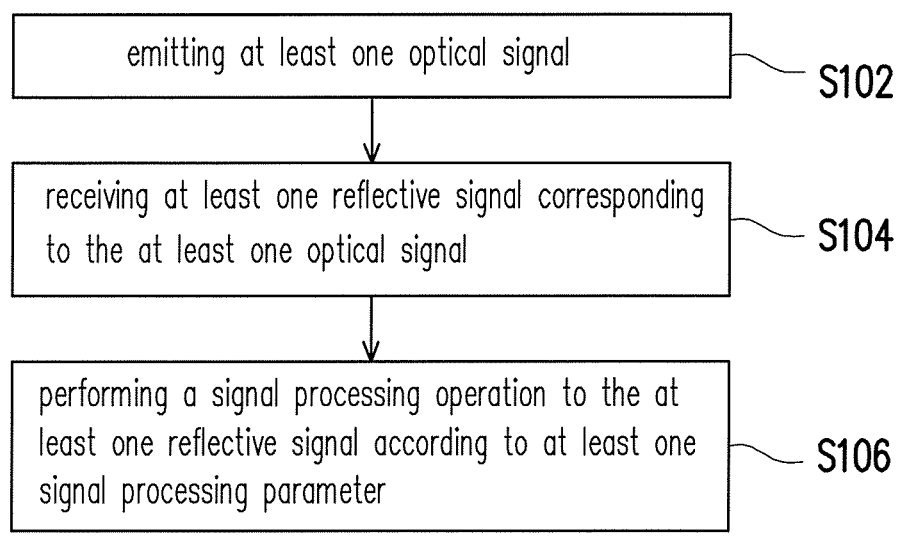
FIG. 12 is a flow chart illustrating an operating method of a wearable device according to an embodiment of the invention.

FIG. 12 is a flow chart illustrating an operating method of a wearable device according to an embodiment of the invention. Please refer to FIG. 12. In the embodiment, the operating method of the aforementioned wearable device 100 may include following steps. At least one optical signal L1 is emitted (step S102). Next, at least one reflective signal R1 corresponding to the at least one optical signal L1 is received (step S104). Next, a signal processing operation is performed to the at least one reflective signal R1 according to at least one signal processing parameter (step S106). The signal processing operation can be referred to in the descriptions above, and will not be repeated herein.

Figure 13:
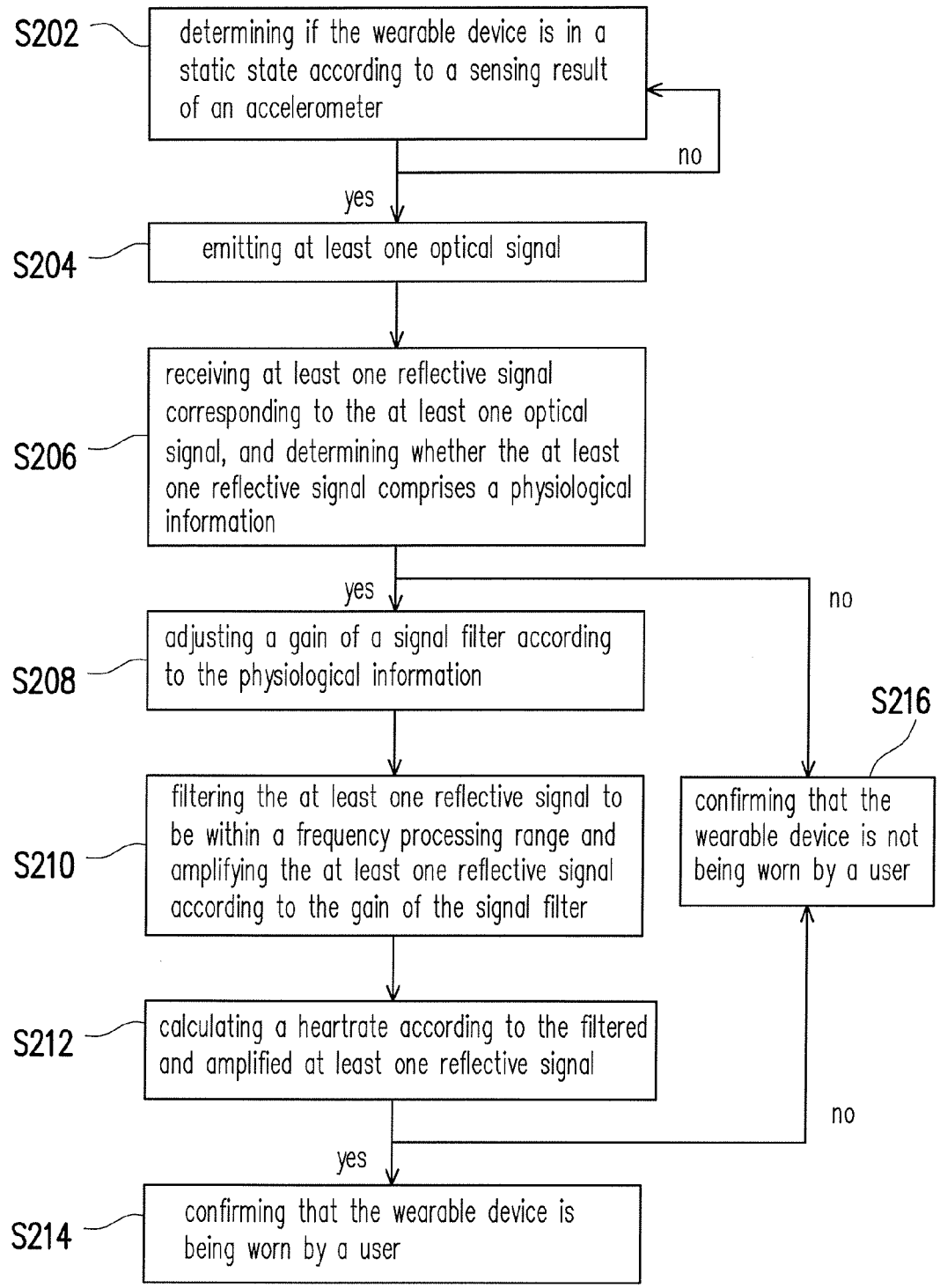
FIG. 13 is a flow chart illustrating an operating method of a wearable device according to another embodiment of the invention.

FIG. 13 is a flow chart illustrating an operating method of a wearable device according to another embodiment of the invention. Please refer to FIG. 13. In the embodiment, the operating method of the aforementioned wearable device 100 may include following steps. First, it is determined if the wearable device 100 is in a static state according to a sensing result of an accelerometer 130 (step S202). The method of determine whether the wearable device 100 is in a static state can refer to the description of the accelerometer 130, and will not be repeated herein. If the wearable device 100 is not in a static state, then keep determining if the wearable device 100 is in a static state (repeating step S202). If the wearable device 100 is determined to be in a static state, then emitting at least one optical signal L1 (step S204). In detail, the optical sensor 120 emits the at least one optical signal L1. The description of emitting the at least one optical signal L1 can be referred to the description of the optical sensor 120, and will not be repeated herein.

Next, at least one reflective signal R1 corresponding to the at least one optical signal L1 is received, and determining whether the at least one reflective signal R1 comprises a physiological information (step S206). In determining if the at least one reflective signal R1 has the physiological information, the description can be referred to the description of the optical sensor 120 and the controller 140, and will not be repeated herein. In particular, the optical sensor 120 receives the at least one reflective signal R1. If the physiological information is not determined, then it is confirmed that the wearable device is not being worn (step S216). If there the physiological information is determined, then next, a gain of a signal filter 142 is adjusted according to the physiological information (step S208). The detailed description of the step of adjusting the gain of the signal filter 142 can be referred to the description of the optical sensor 120 and the controller 140, and will not be repeated herein.

Next, the at least one reflective signal R1 is filtered by the signal filter 142 to be within a frequency processing range and amplified according to the gain of the signal filter (step S210). The detailed description of step S210 can be referred to in the description of the signal filter 142 and the controller 140, and will not be repeated herein.

Next, a heartrate is calculated according to the filtered and amplified at least one reflective signal R1 (step S212). If a heartrate is calculated, then confirming that the wearable device is being worn by a user (step S214). If a heartrate is not able to be calculated, then confirming that the wearable device is not being worn by a user (step S216). The details of the steps S212, S214, and S216 can be referred to in the description of the controller 140, and will not be repeated herein.

To sum up, in the wearable device 100 and the operating method thereof, since the signal processing parameter is adjusted according to the physiological information, the signal processing operation may produce more precise results. Specifically, an optical sensor 120 is included to emit at least one optical signal L1. The at least one optical signal L1 is reflected off different test objects so that the optical sensor 120 receives the at least one reflective signal R1. The at least one reflective signal R1 will have the physiological information for the signal processing parameter to be adjusted. This allows the controller 140 to calculate and produce more precise results.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A wearable device, comprising:
   an optical sensor, adapted to emit at least one optical signal, and receive at least one reflective signal corresponding to the at least one optical signal; and
   a controller, coupled to the optical sensor, and adapted to perform a signal processing operation to the at least one reflective signal according to at least one signal processing parameter, wherein the controller adjusts the at least one signal processing parameter of a signal filter according to physiological information,
   wherein the signal processing operation comprises calculating a raw data of the at least one reflective signal to obtain a moving average, subtracting the moving average from the raw data to obtain a difference, and determining if the difference is greater than a predetermined threshold value,
   wherein when the difference is greater than the predetermined threshold value, the wearable device is in a first usage status, and when the difference is less than the predetermined threshold value, the wearable device is in a second usage status.

2. The wearable device as claimed in claim 1, further comprising:
   an accelerometer, coupled to the controller, and adapted to detect an acceleration of the wearable device,
   wherein the controller determines if the wearable device is in a static state according to a sensing result of the accelerometer, and when the wearable device is in the static state, the controller controls the optical sensor to emit the at least one optical signal, and receive the at least one reflective signal.

3. The wearable device as claimed in claim 1, wherein the signal processing operation comprises performing a Fast Fourier Transformation (FFT) operation towards the at least one reflective signal to identify a peak frequency within a frequency range, wherein when the at least one reflective signal has the peak frequency within the frequency processing range, the wearable device is in a first usage status, and
   when the at least one reflective signal does not have the peak frequency within the frequency processing range, the wearable device is in a second usage status.

4. The wearable device as claimed in claim 1, wherein the controller further comprises the signal filter, wherein the signal filter is adapted to perform the signal processing operation to the at least one reflective signal according to the at least one signal processing parameter, the at least one reflective signal comprises the physiological information,
   wherein the controller sets a frequency processing range of the signal filter according to the physiological information, and the signal filter performs the signal processing operation to the at least one reflective signal within the frequency processing range.

5. The wearable device as claimed in claim 4, wherein when the at least one reflective signal has a peak frequency within the frequency processing range, the wearable device is in a first usage status, and
   when the at least one reflective signal does not have the peak frequency within the frequency processing range, the wearable device is in a second usage status.

6. The wearable device as claimed in claim 4, wherein the controller sets a signal gain of the signal filter according to the physiological information, and the signal filter performs the signal processing operation to the at least one reflective signal according to the signal gain.

7. The wearable device as claimed in claim 6, wherein the optical sensor receives the at least one reflective signal with different intensities when corresponding to a plurality of different test objects, and the controller determines the physiological information of the test objects according to the different intensities of the at least one reflective signal.

8. The wearable device as claimed in claim 7, wherein the at least one optical signal comprises a first optical signal and a second optical signal, respectively becoming a first reflective signal and a second reflective signal when reflecting off the different test objects, wherein an intensity variation of the first reflective signal is greater than an intensity variation of the second reflective signal, and the controller determines the physiological information of the test objects according to the different intensities of the first reflective signal.

9. The wearable device as claimed in claim 8, wherein the controller determines a usage status of the wearable device according to the different intensities of the second reflective signal.

10. A method of operating a wearable device, comprising:
emitting at least one optical signal, and receiving at least one reflective signal corresponding to the at least one optical signal through an optical sensor;
adjusting at least one signal processing parameter of a signal filter according to physiological information of the at least one reflective signal through a controller; and
performing a signal processing operation to the at least one reflective signal according to the at least one signal processing parameter through the controller, wherein performing a signal processing operation to the at least one reflective signal according to at least one signal processing parameter comprises:
calculating a raw data of the at least one reflective signal to obtain a moving average;
subtracting the moving average from the raw data to obtain a difference; and
determining if the difference is greater than a predetermined threshold value,
wherein when the difference is greater than the predetermined threshold value, the wearable device is in a first usage status, and when the difference is less than the predetermined threshold value, the wearable device is in a second usage status.

11. The method as claimed in claim 10, further comprising:
determining if the wearable device is in a static state according to a sensing result of an accelerometer; and
when the wearable device is in the static state, emitting the at least one optical signal, and receiving the at least one reflective signal.

12. The wearable device as claimed in claim 10, performing a signal processing operation to the at least one reflective signal according to at least one signal processing parameter comprises:
performing a Fast Fourier Transformation (FFT) operation towards the at least one reflective signal to identify a peak frequency within a frequency range, wherein when the at least one reflective signal has the peak frequency within the frequency processing range, the wearable device is in a first usage status, and when the at least one reflective signal does not have the peak frequency within the frequency processing range, the wearable device is in a second usage status.

13. The method as claimed in claim 10, further comprising:
setting a frequency processing range of the signal filter according to the physiological information.

14. The method as claimed in claim 13, wherein the step of performing the signal processing operation to the at least one reflective signal according to the at least one signal processing parameter through the controller comprises:
performing the signal processing operation to the at least one reflective signal within the frequency processing range.

15. The method as claimed in claim 14, wherein when the at least one reflective signal has a peak frequency within the frequency processing range, the wearable device is in a first usage status, and
when the at least one reflective signal does not have the peak frequency within the frequency processing range, the wearable device is in a second usage status.

16. The method as claimed in claim 13, wherein the step of adjusting the at least one signal processing parameter of the signal filter according to the physiological information through the controller comprises:
setting a signal gain of the signal filter according to the physiological information.

17. The method as claimed in claim 16, wherein the step of performing the signal processing operation to the at least one reflective signal according to the at least one signal processing parameter through the controller comprises:
performing the signal processing operation to the at least one reflective signal according to the signal gain.

18. The method as claimed in claim 16, wherein in the step of receiving the at least one reflective signal, the at least one reflective signal is received with different intensities when corresponding to a plurality of different test objects, and the method further comprises:
determining the physiological information of the test objects according to the different intensities of the at least one reflective signal.

19. The method as claimed in claim 18, wherein the at least one optical signal comprises a first optical signal and a second optical signal, respectively becoming a first reflective signal and a second reflective signal, when reflecting off the different test objects, wherein an intensity variation of the first reflective signal is greater than an intensity variation of the second reflective signal, and in the step of determining the physiological information of the test objects according to the different intensities of the at least one reflective signal, the physiological information of the test objects is determined according to the different intensities of the first reflective signal.

20. The method as claimed in claim 19, wherein a usage status of the wearable device is determined according to the different intensities of the second reflective signal.

21. A wearable device, comprising:
an optical sensor, adapted to emit at least one optical signal, and receive at least one reflective signal corresponding to the at least one optical signal, wherein the optical sensor receives the at least one reflective signal with different intensities when corresponding to a plurality of different test objects;
a controller, coupled to the optical sensor, and adapted to perform a signal processing operation to the at least one reflective signal according to at least one signal processing parameter, wherein the controller determines physiological information of the test objects according to the different intensities of the at least one reflective signal and adjusts the at least one signal processing parameter of a signal filter according to the physiological information, wherein the signal filter is adapted to perform the signal processing operation to the at least one reflective signal according to the at least one signal processing parameter, the at least one reflective signal comprises the physiological information,
wherein the controller sets a frequency processing range and a signal gain of the signal filter according to the physiological information, and the signal filter performs the signal processing operation to the at least one reflective signal within the frequency processing range according to the signal gain.

* * * * *